US009763837B2

(12) United States Patent
Persson et al.

(10) Patent No.: US 9,763,837 B2
(45) Date of Patent: Sep. 19, 2017

(54) ABSORBENT ARTICLE HAVING FLUID FLOW CONTROL MEMBER

(75) Inventors: Charlotte Persson, Göteborg (SE); Patrik Andersson, Billdal (SE); Kent Vartiainen, Lerum (SE); Charlotta Hanson, Göteborg (SE); Britt-Marie Wiezell, Mölnlycke (SE); Lori-Ann S. Prioleau, St. Paul, MN (US); Thomas R. LaLiberte, Inver Grove Heights, MN (US); Leigh E. Wood, Woodbury, MN (US); Kerstin K. Ehlers, Langenfeld (DE); Peter P. Kitzer, Echt (NL)

(73) Assignee: SCA HYGIENE PRODUCTS AB, Gothenburg (SE)

(*) Notice: Subject to any disclaimer, the term of this patent is extended or adjusted under 35 U.S.C. 154(b) by 21 days.

(21) Appl. No.: 13/308,606

(22) Filed: Dec. 1, 2011

(65) Prior Publication Data
US 2013/0144241 A1 Jun. 6, 2013

(51) Int. Cl.
| A61F 13/537 | (2006.01) |
| A61F 13/15 | (2006.01) |
| A61F 13/538 | (2006.01) |

(52) U.S. Cl.
CPC ...... *A61F 13/53713* (2013.01); *A61F 13/538* (2013.01); *A61F 2013/15406* (2013.01); *A61F 2013/15447* (2013.01)

(58) Field of Classification Search
CPC .............. A61F 13/537; A61F 13/538; A61F 13/15203; A61F 13/5376;
(Continued)

(56) References Cited

U.S. PATENT DOCUMENTS

| 2,399,258 A | 4/1946 | Taylor |
| 2,399,259 A | 4/1946 | Taylor |

(Continued)

FOREIGN PATENT DOCUMENTS

| CN | 1832717 A | 9/2006 |
| CN | 201921003 U | 8/2011 |

(Continued)

OTHER PUBLICATIONS

Notification of Transmittal of the International Search Report (Forms PCT/ISA/220 and PCT/ISA/210) and the Written Opinion of the International Searching Authority (Form PCT/ISA/237) dated Jan. 25, 2013, issued in corresponding International Application No. PCT/US2012/065798. (12 pages).

(Continued)

*Primary Examiner* — Lynne Anderson
(74) *Attorney, Agent, or Firm* — Buchanan Ingersoll & Rooney PC

(57) ABSTRACT

An absorbent article, the absorbent article being a personal hygiene article, comprising a liquid permeable top sheet, a liquid impermeable back sheet, and an absorbent core enclosed between the top sheet and the back sheet, and a fluid flow control member arranged between the top sheet and the backsheet, said fluid flow control member being of a nonwoven material comprising a three dimensional network of fibres, said fibres having a thickness of 200-700 μm, said nonwoven material having a strain of max 50% at 5 kPa.

17 Claims, 2 Drawing Sheets

(58) Field of Classification Search
CPC .. A61F 2013/15406; A61F 2013/15414; A61F 2013/15447; A61F 2013/15325; A61F 2013/15373
USPC .......................................... 604/370, 384, 378
See application file for complete search history.

(56) References Cited

U.S. PATENT DOCUMENTS

| | | |
|---|---|---|
| RE24,906 E | 12/1960 | Ulrich |
| 3,537,121 A | 11/1970 | McAvoy |
| 3,562,079 A | 2/1971 | Steel |
| 3,686,049 A | 8/1972 | Manner et al. |
| 3,687,759 A | 8/1972 | Werner et al. |
| 3,691,004 A | 9/1972 | Werner et al. |
| 3,837,988 A | 9/1974 | Hennen et al. |
| 4,227,350 A | 10/1980 | Fitzer |
| 4,351,683 A | 9/1982 | Kusilek |
| 4,443,513 A | 4/1984 | Meitner et al. |
| 4,610,678 A | 9/1986 | Weisman et al. |
| 4,685,909 A | 8/1987 | Berg et al. |
| 4,769,022 A | 9/1988 | Chang et al. |
| 4,834,735 A | 5/1989 | Alemany et al. |
| 4,988,344 A | 1/1991 | Reising et al. |
| 4,988,345 A | 1/1991 | Reising |
| 5,019,065 A | 5/1991 | Scripps |
| 5,047,023 A | 9/1991 | Berg |
| 5,134,007 A | 7/1992 | Reising et al. |
| 5,147,345 A | 9/1992 | Young et al. |
| 5,296,289 A | 3/1994 | Collins |
| 5,364,382 A | 11/1994 | Latimer et al. |
| 5,439,458 A | 8/1995 | Noel et al. |
| 5,464,491 A | 11/1995 | Yamanaka |
| 5,486,166 A | 1/1996 | Bishop et al. |
| 5,626,571 A | 5/1997 | Young et al. |
| H1698 H | 11/1997 | Lloyd et al. |
| 5,695,868 A | 12/1997 | McCormack |
| 5,700,254 A | 12/1997 | McDowall et al. |
| 5,731,083 A | 3/1998 | Bahia et al. |
| 5,827,254 A | 10/1998 | Trombetta et al. |
| 5,846,230 A | 12/1998 | Osborn, III et al. |
| 5,853,402 A | 12/1998 | Faulks et al. |
| 5,855,999 A | 1/1999 | McCormack |
| 5,861,074 A | 1/1999 | Wu |
| 5,873,867 A * | 2/1999 | Coles et al. ............ 604/368 |
| 5,874,160 A | 2/1999 | Keck |
| 5,879,343 A | 3/1999 | Dodge, II et al. |
| 5,895,379 A | 4/1999 | Litchholt et al. |
| 5,913,850 A | 6/1999 | D'Alessio et al. |
| 5,961,506 A | 10/1999 | Guidotti et al. |
| 5,968,855 A | 10/1999 | Perdelwitz, Jr. et al. |
| 6,030,906 A | 2/2000 | Hassenboehler et al. |
| 6,037,518 A | 3/2000 | Guidotti et al. |
| 6,060,638 A | 5/2000 | Paul et al. |
| 6,096,015 A | 8/2000 | Yeo et al. |
| 6,232,250 B1 | 5/2001 | Palumbo et al. |
| 6,241,714 B1 | 6/2001 | Raidel et al. |
| 6,264,776 B1 | 7/2001 | DiPalma |
| 6,268,544 B1 | 7/2001 | Court et al. |
| 6,312,545 B1 | 11/2001 | Nickel et al. |
| 6,372,952 B1 | 4/2002 | Lash et al. |
| 6,413,338 B1 | 7/2002 | DiPalma |
| 6,417,427 B1 | 7/2002 | Roxendal et al. |
| 6,441,268 B1 | 8/2002 | Edwardsson |
| 6,509,513 B2 | 1/2003 | Glaug et al. |
| 6,515,195 B1 | 2/2003 | Lariviere et al. |
| 6,528,439 B1 | 3/2003 | Stokes et al. |
| 6,545,196 B1 * | 4/2003 | Herrlein ............ A61F 13/51458 604/378 |
| 6,673,982 B1 | 1/2004 | Chen et al. |
| 6,689,933 B1 | 2/2004 | DiPalma |
| 6,700,034 B1 | 3/2004 | Lindsay et al. |
| 6,723,892 B1 | 4/2004 | Daley et al. |
| 6,762,139 B2 | 7/2004 | Strommen |
| 6,808,664 B2 | 10/2004 | Falk et al. |
| 6,844,482 B2 | 1/2005 | Eliasson |
| 6,896,669 B2 | 5/2005 | Krautkramer et al. |
| 7,138,561 B2 | 11/2006 | Fuchs et al. |
| RE39,919 E | 11/2007 | Dodge, II et al. |
| 7,429,689 B2 | 9/2008 | Chen et al. |
| 7,491,354 B2 | 2/2009 | Andersen |
| 2002/0010448 A1 | 1/2002 | Yoshimasa |
| 2002/0022694 A1 | 2/2002 | Wallenwein et al. |
| 2003/0073370 A1 | 4/2003 | Strommen |
| 2004/0041308 A1 | 3/2004 | Topolkaraev et al. |
| 2004/0110442 A1 | 6/2004 | Rhim et al. |
| 2004/0131820 A1 * | 7/2004 | Turner et al. .................. 428/92 |
| 2004/0243078 A1 | 12/2004 | Guidotti et al. |
| 2005/0033253 A1 | 2/2005 | Fuchs et al. |
| 2006/0020250 A1 | 1/2006 | Chester et al. |
| 2006/0094320 A1 | 5/2006 | Chen et al. |
| 2006/0135026 A1 | 6/2006 | Arendt et al. |
| 2006/0148358 A1 | 7/2006 | Hall et al. |
| 2006/0206073 A1 * | 9/2006 | Crane ............... A61F 13/5323 604/378 |
| 2008/0001431 A1 | 1/2008 | Thompson et al. |
| 2008/0132136 A1 | 6/2008 | Uematsu et al. |
| 2010/0105273 A1 | 4/2010 | Motomura et al. |
| 2010/0255258 A1 * | 10/2010 | Curro et al. .................. 428/159 |
| 2010/0280479 A1 * | 11/2010 | Svensson et al. ....... 604/385.23 |
| 2010/0291213 A1 | 11/2010 | Berrigan et al. |
| 2010/0292664 A1 | 11/2010 | Marin |
| 2010/0331804 A1 * | 12/2010 | Larsson .................. 604/385.23 |
| 2013/0143019 A1 | 6/2013 | Wood et al. |
| 2013/0143020 A1 | 6/2013 | Wood et al. |
| 2013/0143462 A1 | 6/2013 | Wood et al. |

FOREIGN PATENT DOCUMENTS

| | | |
|---|---|---|
| EP | 0202127 A2 | 11/1986 |
| EP | 1174464 A2 | 1/2002 |
| EP | 1 504 739 A1 | 2/2005 |
| EP | 2 058 424 A1 | 5/2009 |
| EP | 1153589 A2 | 11/2011 |
| GB | 2 331 937 A | 6/1999 |
| JP | 60-013511 A | 1/1985 |
| JP | H07-502433 A | 3/1995 |
| JP | H10-88454 A | 4/1998 |
| JP | H10-513369 A | 12/1998 |
| JP | 2000-316902 A | 11/2000 |
| JP | 3161588 | 4/2001 |
| JP | 2003-521955 A | 7/2003 |
| JP | 2003-260081 A | 9/2003 |
| JP | 2005-307386 A | 11/2005 |
| JP | 2005-537399 | 12/2005 |
| JP | 2005-537399 A | 12/2005 |
| JP | 2005-537405 | 12/2005 |
| JP | 2005-537405 A | 12/2005 |
| RU | 2140855 | 11/1999 |
| WO | 93/11726 A1 | 6/1993 |
| WO | 9516562 | 6/1995 |
| WO | 96/16622 A1 | 6/1996 |
| WO | 96/37644 A2 | 11/1996 |
| WO | 97/47263 A1 | 12/1997 |
| WO | 99/27879 A2 | 6/1999 |
| WO | 00/19955 A2 | 4/2000 |
| WO | 03/015914 A1 | 2/2003 |
| WO | 2004/020710 A1 | 3/2004 |
| WO | 2004/020711 A1 | 3/2004 |
| WO | 2008/108238 A1 | 9/2008 |
| WO | WO 2009/008788 A1 | 1/2009 |
| WO | 2010/056835 A2 | 5/2010 |

OTHER PUBLICATIONS

Notification of Transmittal of the International Search Report (Forms PCT/ISA/220 and PCT/ISA/210) and the Written Opinion of the International Searching Authority (Form PCT/ISA/237) dated Feb. 20, 2013, issued in corresponding International Application No. PCT/US2012/067187. (12 pages).

(56) References Cited

OTHER PUBLICATIONS

Notification of Transmittal of the International Search Report (Forms PCT/ISA/220 and PCT/ISA/210) and the Written Opinion of the International Searching Authority (Form PCT/ISA/237) dated Apr. 8, 2013, issued in corresponding International Application No. PCT/US2012/065801. (12 pages).
Notification of Transmittal of the International Search Report (Forms PCT/ISA/220 and PCT/ISA/210) and the Written Opinion of the International Searching Authority (Form PCT/ISA/237) dated Jul. 5, 2012, issued in corresponding International Application No. PCT/SE2011/051462. (14 pages).
US Official Action dated Jul. 3, 2013 issued in co-pending U.S. Appl. No. 13/308,962.
US Official Action dated Jul. 5, 2013 issued in co-pending U.S. Appl. No. 13/308,936.
US Official Action dated Jul. 23, 2013 issued in co-pending U.S. Appl. No. 13/308,996.
US Official Action dated Jan. 29, 2014 issued in co-pending U.S. Appl. No. 13/308,936.
US Final Official Action dated Feb. 5, 2014 issued in co-pending U.S. Appl. No. 13/308,996.
US Final Official Action dated Nov. 5, 2013 issued in co-pending U.S. Appl. No. 13/308,962.
US Final Official Action dated Oct. 3, 2013 issued in co-pending U.S. Appl. No. 13/308,936.
US Official Action dated Feb. 18, 2015 issued in co-pending U.S. Appl. No. 13/308,996.
US Advisory Action dated Jul. 3, 2014 issued in co-pending U.S. Appl. No. 13/308,996.
Chinese Notification of the First Office Action dated Dec. 16, 2014 issued in co-pending Chinese Patent Application No. 201180075200.8 and English translation (9 pages).
US Official Action dated Jun. 17, 2015 issued in co-pending U.S. Appl. No. 13/308,996 (22 pages).
Hydrophilic; Textile Glossary, Celanese Acetate, copyright 2001 (3 pages).
US Official Action dated Apr. 7, 2015 issued in co-pending U.S. Appl. No. 13/308,936.
US Official Action dated Aug. 27, 2015 issued in co-pending U.S. Appl. No. 13/308,936 (13 pages).
Japanese Notice of Reasons for Rejection dated Jun. 1, 2015 issued in the corresponding Japanese Patent Application No. 2014-544703 and English translation (6 pages).
European Supplementary Search Report dated Jun. 18, 2015 issued in the corresponding European Patent Application No. 11876788.8-1308 (6 pages).
Office Action issued on Apr. 28, 2016, by the State Intellectual Property Office of China in corresponding Chinese Patent Application No. 201280058803.1, and English translation of the Office Action. (20 pages).
Decision on Grant issued in corresponding Russian Patent Application No. 2014126579, dated Sep. 30, 2015, with English translation. (13 pages).
Final Office Action issued on Sep. 6, 2016, by the United States Patent and Trademark Office in co-pending U.S. Appl. No. 13/308,936. (13 pages).
Office Action (Notification of Reasons for Refusal) issued on Jan. 10, 2017, by the Japanese Patent and Trademark Office in corresponding Japanese Patent Application No. 2014-544774 and English Translation of the Office Action. (5 pages).
First Office Action issued on Nov. 4, 2016, by the Japanese Patent Office in Japanese Patent Application No. 2014-544775. (3 pages).
Office Action (Notification of Reasons for Refusal) dated Jan. 10, 2017, by the Japanese Patent and Trademark Office in corresponding Japanese Patent Application No. 2014-544774 and English Translation of the Office Action. (5 pages).
Office Action dated Apr. 28, 2017, by the Canadian Patent Office in corresponding Canadian Patent Application No. 2,856,052. (4 pages).

* cited by examiner

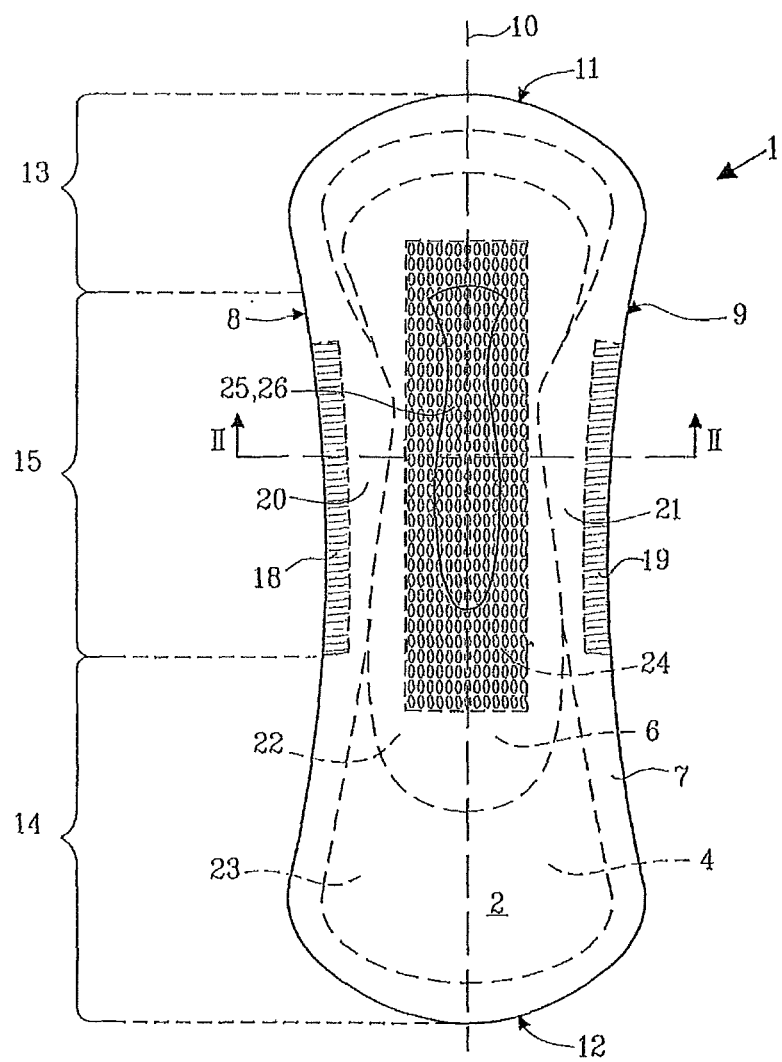
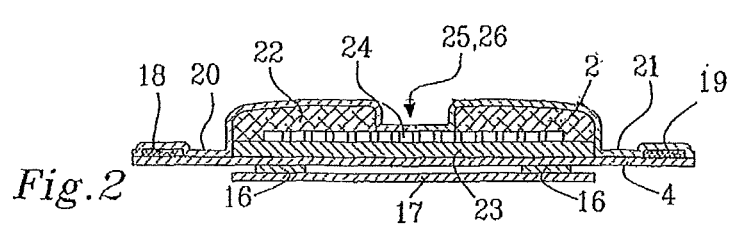

ABSORBENT ARTICLE HAVING FLUID FLOW CONTROL MEMBER

TECHNICAL FIELD

The present invention pertains to an improved absorbent article comprising a fluid flow control member.

BACKGROUND ART

Absorbent articles for hygiene purposes are typically intended to absorb body liquids, such as urine and blood. Users put high demands on such articles, requiring them to be thin and comfortable and at the same time to effectively absorb body liquids.

Absorbent articles, such as sanitary napkins, diapers, incontinence guards or the like typically include a liquid pervious topsheet, intended to be facing the wearer during use, a liquid impervious backsheet and an absorbent structure there between. Absorbent structures commonly used are relatively thin and compressed, and often include a high amount of so called superabsorbents, which have a high absorption capacity but in many cases a too low absorption speed in order to instantaneously be able to absorb the large amount of liquid that can be discharged during a few seconds of urination. Therefore, a liquid acquisition layer is commonly incorporated as it has the ability to quickly receive large amounts of liquid, to distribute it and temporarily store it before it is absorbed by the absorbent structure. An example of an absorbent article comprising a liquid acquisition layer is disclosed in GB 2331937A.

It is important that the liquid acquisition layer has sufficient liquid distributing capacity, in order to avoid leakage, and to fully get use of the absorption capacity of the absorbent article. There is still a need for improvement of the liquid acquisition properties of hygiene absorbent articles, in order to enhance fluid flow control in the articles.

SUMMARY OF THE INVENTION

The object of the invention is to provide an absorbent article having improved fluid flow control properties. This is achieved by the absorbent article as defined in claim 1.

The present invention thus relates to an absorbent article, the absorbent article being a personal hygiene article, comprising a liquid permeable top sheet, a liquid impermeable back sheet, and an absorbent core enclosed between the top sheet and the back sheet, and a fluid flow control member arranged between the topsheet and the backsheet, said fluid flow control member is of a nonwoven material comprising a three dimensional network of fibres, said fibres having a thickness of 200-700 µm, said nonwoven material having a strain of max 50% at 5 kPa. The material characteristics of the fluid flow control member lead to a relatively low strain, which in turn ensures that there is always a free volume in the fluid flow control member, so that body liquids are effectively distributed also when a pressure is exerted on the article, as is the case during use, especially when sitting down.

BRIEF DESCRIPTION OF THE DRAWINGS

FIG. 1 shows an example of an absorbent article according to the invention, seen from the side which will be facing the user when it is being worn.

FIG. 2 shows a cross-sectional view of the absorbent article of FIG. 1, along the line II-II.

DETAILED DESCRIPTION OF THE INVENTION

Figure 3:
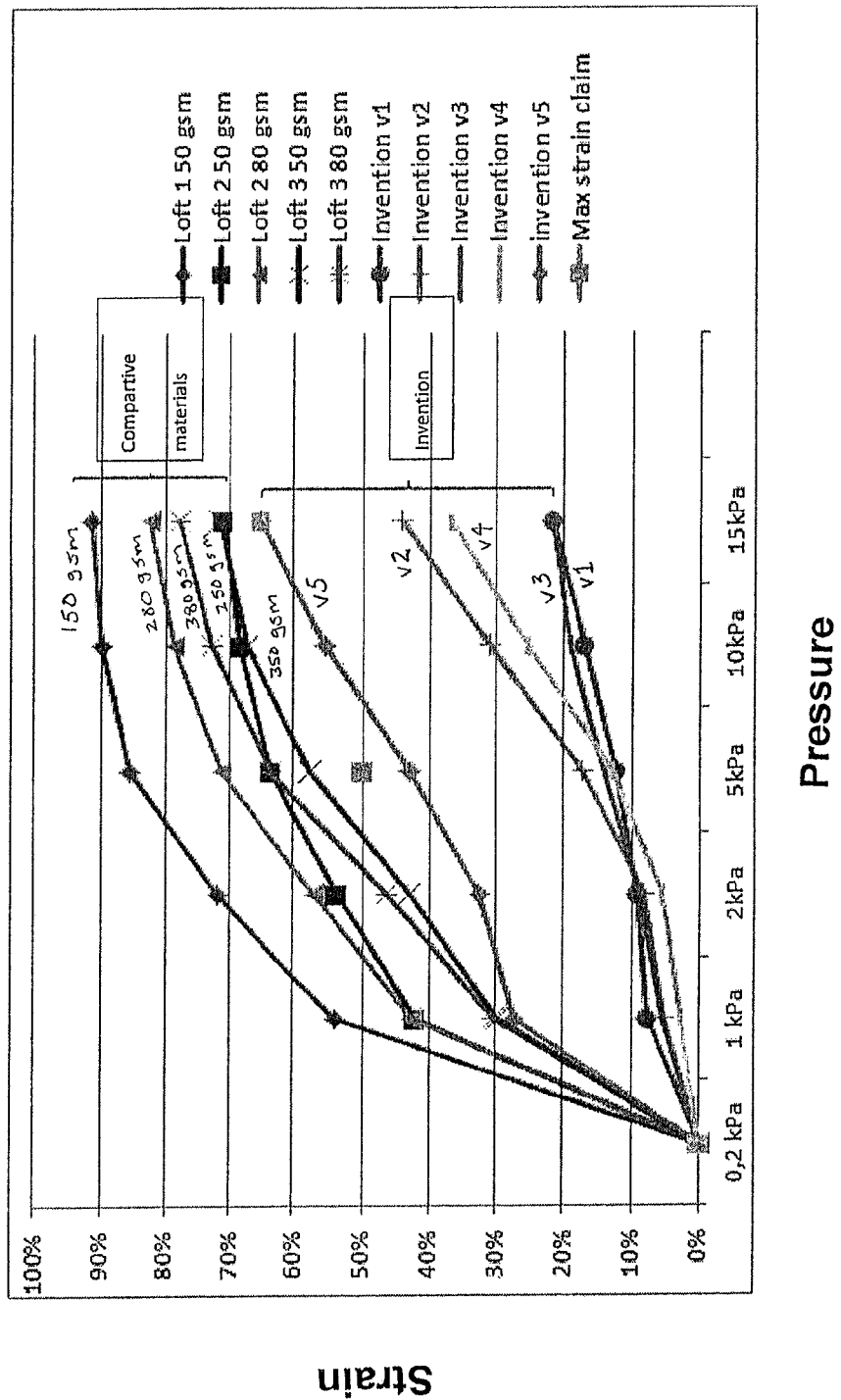
FIG. 3 is a graph presenting the result of a strain test.

The absorbent article of the invention being a personal hygiene article may be any type of absorbent personal hygiene article, such as incontinence protectors, sanitary napkins, panty liners, diapers with tape fasteners, pant diapers or belted diapers.

The absorbent article comprises a liquid permeable topsheet, a liquid impermeable backsheet, and an absorbent core enclosed between the topsheet and the backsheet, and a fluid flow control member arranged between the topsheet and the backsheet. The fluid flow control member is of a nonwoven material comprising a three dimensional network of fibres, which fibres have a thickness of 200-700 µm. The nonwoven material of the fluid flow control member has a strain of max 50% strain at 5 kPa. The strain of the nonwoven material is a measure of how resistant the material is to compression, and expresses the relative compression of the material at a certain pressure exerted thereon, the lower the strain of the material is, the higher is the resistance to compression. The material of the fluid flow control member of the invention is more compression resistant than materials that have previously been used for fluid flow control in absorbent articles. The low strain ensures that the fluid flow properties of the fluid flow control member are maintained during use of the absorbent article. The compression resistance is obtained by the "Mecano method" for determining strain as described below, which uses Instron "Bluehill" software.

When a hygiene absorbent article is used by a wearer, it is exposed to pressure, which tends to compress the article. Such pressures are typically about 2-5 kPa when standing or walking, about 10-20 kPa when sitting, 30 kPa when sitting and leaning forward, and up to 50 kPa when bicycling, in the centre of an absorbent pad. In order to maintain excellent liquid distribution properties in the absorbent article, it is important that the fluid flow control member can withstand such pressure.

The parameters of the material of the fluid flow control member of the invention ensure a porous material in which a free volume is present, also when the absorbent article is exposed to pressure exerted by a user wearing the article, as a result of high resistance to compression. Due to the free volume the fluid flow control member can accommodate a relatively large liquid volume. Thus, body liquids discharged can be effectively received into to the fluid flow control member, and can flow inside it to different parts of the absorbent core, where it is absorbed, and accordingly the risk of leakage is minimised.

In addition, the open structure of the porous fluid flow control member material will promote air circulation, and thereby lower the temperature in the absorbent article, which is good for the wearer's skin.

The nonwoven material of the fluid flow control member preferably has a strain of max 65% at 15 kPa, preferably max 45% at 15 kPa, in order to further enhance the fluid flow control properties.

The fibres of the nonwoven material of the fluid flow control member preferably have a thickness of 250-650 µm, preferably 300-600 µm, in order to obtain enough compression resistance. The cross section of the fibres is preferably substantially solid and may be uniform along the length of the fibre and may be of any shape, such as circular or non-circular, e.g. square or rectangular. The diameter of the fibres may be measured using measuring means in a microscope. The diameter should be measured at the largest dimension and cross section of the fibres.

The network of fibres forms an open network of macropores defined by the nonlinear fibres. The pores are random in size and in orientation throughout the material. The nonwoven material preferably has a porosity of at least 0.85 at a compression pressure below 15 kPa. Further, the nonwoven material of the fluid flow control member preferably has a basis weight of 200-900 g/m$^2$, preferably 200-700 g/m$^2$. Suitably, the fluid flow control member has a total free volume of at least 20 ml, to ensure prevention of leakage. The fluid flow control member advantageously has a thickness of 4-20 mm, preferably 5-10 mm at 0.2 kPa, preferably 2-7 mm at 15 kPa, to function well and be comfortable to wear. The member may have a width of less than 40 mm, such as 30-40 mm. The length of the member may be less than 150 mm, such as 120-150 mm.

The insert may for example have a size of about 30×120×8 mm to fit properly in the crotch area. The density of the fluid flow control member may be 0.01 to 0.10 g/cm$^3$, preferably 0.03 to 0.10 g/cm$^3$ at 0.2 kPa.

The fluid flow control member may consist of a single nonwoven material layer and is preferably substantially free from absorbing fibres and superabsorbent material. The non-woven material is preferably made of substantially continuous fibres. Substantially continuous fibres herein means continuous fibres including unintentional and accidental breaks of the fibres made during the manufacturing of the nonwoven material. The fibres are preferably mainly continuous to reduce the risk of fibre penetration through the product surface hurting the wearer and in order to decrease particle contamination in the converting process. The network of fibres in the fluid flow control member may be so called "coiled" fibres which may be produced by techniques such as melt-extrusion followed by cooling the fibres resulting in bonds between the coiled fibres. The coils may be randomly orientated, but may be orientated in a primary direction as a result of the manufacturing process, i.e. in the machine direction of the melt extrusion process and the subsequent cooling step.

The non-woven material of the fluid flow control member preferably comprises thermoplastic polymer fibres, preferably selected from but not limited to, polyesters, polyamides and polyolefins such as polyethylenes and polypropylenes, and may be a mixture of any of these. The non-woven material may also contain surfactant to facilitate liquid penetration in order to be drained quickly and not hold any liquid, thus maintaining free volume capacity for the next gush of liquid.

The fluid flow control member may advantageously include a supporting carrier layer, preferably of a nonwoven material or a film material to facilitate converting and holding with vacuum during production. Further the nonwoven material of the fluid flow control member can be folded to have a tube-like configuration, in order to avoid sharp edges and to create extra free volume therein. The fluid flow control member may comprise one or more compressed lines to facilitate folding.

The fluid flow control member may be made of a nonwoven material in which the fibres preferably are bonded, preferably melt-bonded, as obtained during the manufacturing process, at points where fibres intersect. A bonded nonwoven has the advantage of being more resistant to compression, ensuring excellent liquid flow through the material. Alternatively, the fluid flow control member may be made of a bonded, stretched and thereafter relaxed nonwoven material. Such material having bonded and, in addition, random broken bonding points where fibres intersect. The material is achieved by stretching a bonded nonwoven material until random bonding points break. The mechanical integrity of the material is still sufficient and the material performs well and has the advantage that less material may be used. Such material may be stretched in a direction parallel to the primary direction of the fibres as described above in order to obtain an elongation of the material and a more controlled breakage of bonding points. The elongation of the material may be at least 25%.

The stretched material may comprise at least 1, 2, or 3 broken bonding points per 1 cm$^3$. The distribution of broken bonding points may be uniformly distributed through the material. The stretched material may typically exhibit microscopic evidence that prior filament to filament bonding points have been broken. Thus, the number of broken bonds per cm$^3$ may be counted microscopically.

The topsheet and the backsheet of the absorbent article may extend together laterally outside of the absorbent core along the whole circumference of the absorbent core and be connected to each other in an edge joint around the periphery of the absorbent core. The backsheet may preferably cover part of the topsheet to form an edge barrier. The edge joint may be formed in any suitable manner as known in the art such as by means of adhesive, ultrasonic bonding, thermo-bonding, stitching, etc. Alternative covering arrangements such as wrapped-around covers are also conceivable within the scope of the invention.

The topsheet may consist of any material which is suitable for the purpose, i.e. be soft and liquid pervious. Examples of commonly found topsheet materials are nonwoven materials, perforated plastic films, plastic or textile mesh, and fluid permeable foam layers. Laminates consisting of two or more topsheet materials are also commonly employed, as are top sheets consisting of different materials within different parts of the fluid permeable wearer-facing surface.

The backsheet is fluid impermeable. However, backsheet materials that are only fluid repellant may be used particularly in instances where relatively small amounts of urine are expected to be taken up. The backsheet is commonly constituted by a thin, flexible, fluid-impermeable plastic film, but fluid-impermeable nonwoven materials, fluid impermeable foams and fluid impermeable laminates are also contemplated within the scope of the invention. The backsheet may preferably be breathable, implying that air and vapor may pass through the backsheet. Furthermore, the backsheet may have an outer, garment-facing surface of a textile material such as nonwoven.

The absorbent core may be made up of any suitable absorbent or fluid uptake material as known in the art, such as one or more layers of cellulose fluff pulp, foam, fibre waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. An absorbent structure may comprise 40-80% superabsorbents and 60-20% pulp fibres.

The absorbent core may further incorporate components for improving the properties of the absorbent core. Some examples of such components are binder fibers, fluid-dispersing materials, wetness indicators, fluid acquisition materials, etc., as known in the art.

The absorbent article typically, in case of a pad or a sanitary napkin, has an elongate, generally rectangular shape when fully extended in all directions. In this context, a generally rectangular shape is intended to encompass also that, for instance, the corners of the absorbent article may be rounded, or that the edges of the absorbent article may not be completely linear. Accordingly, any suitable shape may be used for the absorbent article, such as hourglass shape, trapezoidal shape, triangular shape an oval shape, etc. The shape of the article of the invention may be symmetrical about a transverse center line through the article, or may be asymmetrical with end portions having differing shapes and/or differing sizes.

The absorbent article may have two longitudinal side edges having equal length and extending generally in the same direction as a longitudinal center line through the absorbent article. Front and rear end edges typically extend transversely to the longitudinal center line at the ends of the absorbent article. The rear end edge is intended to be orientated rearwards during use of the absorbent article, and the front end edge is intended to be facing forwards towards the abdomen of the wearer.

The absorbent article may have a front end portion, a rear end portion and a crotch portion located intermediate the end portions, the crotch portion being a portion, which is intended to be placed against the crotch of a wearer during use of the article and to constitute the main acquisition area for body fluid that reaches the absorbent article.

The absorbent article may further include fastening means for fastening of the absorbent article inside a supporting pant garment, such as a pair of underpants. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent article in the supporting pant garment, the protective layer is removed from the fastening means to expose the adhesive and make it available for fastening to the pant garment.

Elastic elements may be arranged along the side edges laterally outside the absorbent core. The elastic elements may be bands of elastic material. The elastic elements are optional components of the absorbent article of the invention and may be omitted.

The fastening means is optional to the invention and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means may be a mechanical fastener such as hook-type fasteners, clips, press studs, etc. or may be a frictional fastener such as a frictional coating or an open-celled foam. Combinations of different types of fasteners are also conceivable.

The fluid control member may be situated above or below an absorbent core, but preferably above an absorbent core. The absorbent core of the absorbent article preferably comprises a first absorbent layer and a second absorbent layer. The fluid flow control member may be arranged in the absorbent article between the first absorbent layer and the second absorbent layer. The first absorbent layer may be placed beneath and in direct contact with the topsheet, or may alternatively be placed in indirect contact with the topsheet through one or more intervening components such as tissue layers, acquisition layers or further absorbent layers. Similarly, the second absorbent layer may be placed directly beneath the fluid flow control member and in direct contact with the fluid flow control member and the backsheet, or may be in indirect contact with one or both of those components by intervening components. By arranging the fluid flow control member between the first and second absorbent layers, it forms a channel in the absorbent article and leads the fluid to the back and front of the article. The contact area between the fluid flow control member and the absorbent core increases which facilitates distribution and rapid absorption of liquid in the article. The fluid flow control member may be smoothened or flattened in order to obtain process advantages and prevent discomfort for the user.

The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibres and superabsorbent material, wherein the ratio of superabsorbent material to fibres may vary in the layer.

The first and second absorbent layers may have any suitable shape, such as an hourglass shape with widened end portions and a narrow portion in the crotch portion, or a rectangular shape. The second absorbent layer may be placed beneath the first absorbent layer and may be somewhat smaller than the first absorbent layer. The first absorbent layer may extend further forward and rearward in the absorbent article than the second absorbent layer. Moreover, the second absorbent layer may be omitted in the absorbent article according to the invention or the article may comprise one or more further absorbent layers.

The first absorbent layer advantageously has an opening extending completely through the layer in the crotch portion of the absorbent article, thereby forming a cavity in the article. The opening preferably has elongate shape, approximately mimicking the shape of the absorbent layers.

The topsheet preferably extends down into the cavity that is defined by the opening in the first absorbent layer and the surface of the fluid flow control structure that is facing the topsheet. Thereby, the cavity will be lined with topsheet material and will be accessible from the outer body facing surface of the absorbent article. The cavity is advantageously located in the wetting area of the absorbent article and will then in use be placed directly beneath the urethra and the vaginal opening of a female wearer. Accordingly, any body fluid that is released to the absorbent article will flow into the cavity and be distributed further into and throughout the absorbent core.

A part of the fluid that is collected in the cavity may be absorbed by the first absorbent layer through the walls of the cavity. However, the major part of the fluid will continue downward in the absorbent article, through the bottom of the cavity and into the fluid flow control member where it is distributed longitudinally and laterally along the flow control member.

The fluid flow control member may be of rectangular shape and may be surrounded in the longitudinal and lateral directions by portions of the absorbent core. Other shapes and configurations for the fluid flow control structure may also be used. However, it is generally advantageous if the fluid flow control member has smaller width and is shorter than the absorbent core, as this facilitates distribution to a large area of the absorbent core. One or more compressed lines, acting as hinges, may advantageously be arranged in the fluid flow control member, which is relatively stiff to facilitate folding of the absorbent article.

The invention will now be described by means of example referring to FIGS. 1-2. In this example of the invention the absorbent article is a urine incontinence protector 1. In FIG. 1, the absorbent article is seen from the side of the absorbent article that is intended to be facing towards a wearer's body when being worn, and in FIG. 2, it is seen in cross-section along the line II-II in FIG. 1. The absorbent article 1 comprises a fluid permeable topsheet 2, disposed at the top surface of the absorbent article 1 which is intended to be facing a wearer of the absorbent article 1, a fluid impermeable backsheet 4 disposed at the lower back side of the incontinence protector 1 that is intended to be facing the undergarment of the wearer, and an absorbent core 6, enclosed between the topsheet 2 and the backsheet 4.

The topsheet 2 and the backsheet 4 of the incontinence protector 1 extend together laterally outside of the absorbent core 6 along the whole circumference of the absorbent core 6 and are connected to each other in an edge join 7 around the periphery of the absorbent core 6. The two longitudinal side edges 8, 9 of the absorbent article have equal length and extend generally in the same direction as a longitudinal centre line 10 through the absorbent article 1. Front and rear end edges 11, 12 extend transversely to the longitudinal centre line 10 at the ends of the incontinence protector. The incontinence protector 1 has a front end portion 13, a rear end portion 14 and a crotch portion 15 located intermediate the end portions 13, 14, the crotch portion 15 being intended to be placed against the crotch of a wearer during use and to constitute the main acquisition area for body fluid that reaches the absorbent article 1.

The incontinence protector 1 may further include a fastening means 16 for fastening of the incontinence protector 1 inside a supporting pant garment, such as a pair of underpants. The fastening means 16 is in the form of two longitudinally extending bands of pressure sensitive adhesive arranged on the garment-facing surface of the backsheet 4. In FIG. 2, the fastening means 16 can be seen to be covered by a releasable protective layer 17. Elastic elements 18, 19 in the form of bands of elastic material may also be arranged along the side edges 8, 9 in the side flaps 20, 21 formed by portions of the topsheet 2 and backsheet 4 extending laterally outside the absorbent core 6 to improve the anatomical fit of the incontinence protector.

The absorbent core 6 comprises a first absorbent layer 22 and a second absorbent layer 23. A fluid flow control member 24 is arranged between the first absorbent layer 22 and the second absorbent layer 23. In this example, the first absorbent layer 22 is placed beneath and in direct contact with the topsheet 2.

The first absorbent layer 22 has an opening 25 extending completely through the absorbent layer 22 in the crotch portion 15 of the incontinence protector 1. The opening 25 has an elongate shape, mimicking the shape of the absorbent layers 22, 23. The topsheet 2 extends down into the cavity 26 that is defined by the opening 25 in the first absorbent layer 22 and the topsheet-facing surface of the fluid flow control member 24. The cavity 26 is located in the wetting area of the incontinence protector 1 and will in use be placed directly beneath the urethra and the vaginal opening of a female wearer. Any body fluid that is released to the incontinence protector 1 will directly flow into the cavity 26 and be distributed further into and throughout the absorbent core 6 via the fluid control member 24.

Experiments

A number of different materials have been compression tested, to compare the strain of commonly used liquid acquisition distribution materials, being high lofts of air through bonded nonwoven, with materials used for the fluid flow control member of the present invention. These tests were performed by the methods as described here below.

Porosity

The porosity at a certain compression load on the sample was estimated by means of the following equations and methods:

$$\text{Porosity} = 1 - \frac{\text{Basis weight of material}\left(\frac{g}{cm2}\right)}{\text{Thickness of material at actual load (cm)(Fiber density}\left(\frac{g}{cm3}\right)\text{)}}$$

Fiber density in this case is the density of the fibers, including pores or holes in a hollow fiber. Fiber density=(weight per unit length of fiber (g/cm))/(cross sectional area of the fiber including pores ($cm^2$)).

Cross sectional area of a circular fiber including pores is $\pi r^2$ ($cm^2$), were r is the radius of the fiber. Weight per unit length of fiber can be taken as the measure of the denier of the fiber expressed in grams per centimeter. Thickness at the actual pressure is measured by means of the Mecano method disclosed herein.

In case the material is made up of different fibers the average fiber density is used: Average fiber density=$1/\Sigma(x_i/\rho_i)$ where $x_i$ is the weight ratio of the actual fiber quality and $\rho_i$ is the density of the actual fiber. $\Sigma$ denotes the sum over all components i in the sample.

Strain (Mecano-Method)

Procedure:

The principle of the method is to slowly compress a material with a metal rod to a force of 5 N while continuously measuring the thickness of the material. The result consists of the data points for force and extension. The force translates to a pressure given the contact area of the rod. The metal rod is cylindrical and has a diameter of 10 mm with a flat base having a diameter >7 cm. The rod is mounted in a 10 N load cell in the upper fixture of an Instron testing apparatus. A flat plate is mounted in the bottom fixture and is centered under the rod to that a sample may be placed on top of the plate and be compressed without movement of the plate. The rate of movement of the rod is 5 mm per minute. These settings have been pre-programmed into an Instron Bluehill program called "New Mecano 5 N", but before running a test, the program settings should be checked in order to make sure that all limits are set to their proper values. Running with a modified version could lead to damage to the equipment, especially the sensitive load cell.

Running a Test:

The first run is an empty run without a sample. This run is used to find the zero thickness position, which is where the steel plate stops the rod. The empty run typically generates forces higher than the maximum limit set before the rod stops, because of the rapid increase in force that occurs when the rod impacts the metal and for which the apparatus cannot compensate sufficiently quickly. Care should be taken to ascertain that the load cell can withstand the impact without being damaged. Special settings can be used for the empty run to lower the limiting maximum force and the speed of the rod.

When the rod stops, the Instron equipment awaits user input. The extension is then manually reset to zero. This ensures that the extension is set to zero at the exact correct point where the rod touches the base and the extension is measured relative to the bottom plate. The rod may thereafter be manually moved up so that a sample can be placed on the lower plate.

To test a sample, the rod is moved manually so that it is above the surface of the sample and the program is started. The rod moves down at a speed of 5 mm per minute until the limiting force is reached.

Samples:

The samples are squares with 50 mm sides punched from the tested material. Samples were taken, if the material was of uneven thickness, from the thickest parts of the material. The rod is pressed into the centre of the sample and each sample is tested three times without being moved between runs. Ten samples of each tested material are used, giving thirty measurements in total including the empty run, thirty-one test runs are made for each tested material.

Results:

The result is the complete set of data points for force versus extension. The force is recalculated into pressure using the force measured divided by the bottom area of the rod. The result may be plotted and reported or a specific pressure may be chosen and the thickness noted, so that the result is a thickness for a given pressure. The strain is the relative compression of the material when the pressure is raised from a reference pressure level to a final pressure level, i.e. strain (%)=(original thickness)−(final thickness)/(original thickness). Original thickness, i.e. 0% strain is measured at a pressure of 0.2 kPa and final thickness is measured at a pressure of 15 kPa.

Fibre Thickness

The thickness (in micrometers) of the fibres in the nonwoven material was measured manually in a light microscope using the diameter measuring tool on the microscope. Cut filament ends were measured. The fibre thicknesses mentioned herein is an average of 10 measurements.

The materials tested were as indicated below in Table 1.

The results of the test are presented in Table 1 and in the graph of FIG. 3, wherein the five uppermost lines represent the conventional loft materials tested (Comparative materials) and the five lower lines represent the materials of the invention. These results show that there is a pronounced difference in the compression of the materials used in the invention, expressed in percent of the original sample thickness, as compared to hitherto commonly used materials. The samples representing the invention have significantly higher compression resistance than the prior art material, showing that they can withstand pressures normally exerted by a wearer during normal use without any substantial compression of the nonwoven material. It is to be noted that both the bonded and the substantially non-bonded material according to the invention may withstand the high pressures. The results also show that the bonded non-woven materials have particularly good strain properties for the purposes of the invention.

TABLE 1

| Sample | Material | Basis weight g/m² | Fibre thickness (µm) | Material thickness (mm) at 0.2 kPa ref | 5 kPa | 15 kPa |
|---|---|---|---|---|---|---|
| Loft 1 50 | PET + PP staple fibers | 50 | mix of 22 µm and 43.6 µm | 4.5 | 0.6 | 0.38 |
| Loft 2 50 | As above | 50 | As above | 1.2 | 0.4 | 0.35 |
| Loft 2 80 | As above | 80 | As above | 5.2 | 1.5 | 0.92 |
| Loft 3 50 | As above | 50 | As above | 2 | 0.9 | 0.58 |
| Loft 3 80 | As above | 80 | As above | 4.8 | 1.8 | 1.07 |
| Invent. v1 | Continuous polyolefin fibers bonded | 640 | 444 µm | 6.1 | 5.4 | 4.80 |
| Invent. v2 | As above | 499 | 388 µm | 7.7 | 6.3 | 4.26 |
| Invent. v3 | As above | 673 | 564 µm | 7.5 | 6.4 | 5.85 |
| Invent. v4 | As above | 541 | 413 µm | 7.3 | 6.4 | 4.60 |
| Invent. v5 | Continuous Polyolefin fibers bonded and having random broken bondings | 265 | 428 µm | 9 | 5.2 | 3.16 |

Flow Rate Measurements

The flow rate in a steady state situation through a fluid flow control member according to the invention and a standard high loft was measured in the following way.

Sample materials had the dimensions 30×150 mm and a material thickness of about 4 mm at 0.2 kPa. Each sample material was wrapped in a water tight film. One transverse side edge (with dimension 30×4 mm) was sealed but the other transverse side edge was left open. A window was cut out of the film at the top end of the sample. The window cut out was 20×50 mm. The sample was subjected to a load of 4.5 kg which for this sample size equals 10 kPa. An 8 mm water pillar was kept constant during the measurement and the liquid flow through the sample was measured. The pressure is applied to the sample via a plexiglass plate with holes above the window and the liquid flow is recorded by a scale. A float is immerged in a bath and connected to the scale via a fixed arm. This allows for continuous registration of the flow during the test. Liquid was applied through the window opening and flowed through the sample towards the open transverse end of the sample material

TABLE 2

Flow rate in ml/s (slopes of ART graphs at equilibrium)

| Sample | Invention v2 | Loft 1 50 |
|---|---|---|
| 1 | 7.2 | 0.3 |
| 2 | 8.6 | 0.4 |
| 3 | 7.6 | 0.4 |
| Average | 7.8 | 0.4 |

The flow rate through a fluid flow control member according to the invention under 10 kPa pressure was 7.8 ml/s compared to 0.4 ml/s for a standard high loft. The difference in flow rate is substantial. This should be obvious by any method measuring flow rate under pressure.

Hence, an absorbent article of the invention including a fluid flow control member will maintain its excellent fluid distribution properties also when exposed to pressure exerted by a wearer. Thus, substantially lower leakage is obtained according to the article of the invention compared to articles having a standard high loft as commonly used within the art.

The invention claimed is:

1. An absorbent article, the absorbent article being a personal hygiene article that is wearable by a user and has a garment-facing side and a skin facing side, comprising a liquid permeable top sheet, a liquid impermeable back sheet, and an absorbent core enclosed between the top sheet and the back sheet, and a fluid flow control member arranged between the top sheet and the back sheet, wherein said fluid flow control member is substantially free from absorbing fibres and superabsorbent material, and wherein said fluid flow control member has a thickness of 4-20 mm and consists of only a single nonwoven material layer comprising a three dimensional network of fibres, said fibres being randomly oriented, and having a thickness of 200-700 µm, said nonwoven material having a basis weight above 300 $g/m^2$ and less than or equal to 900 $g/m^2$, having a total free volume of at least 20 mL, and having a maximum strain of 50% at a pressure of 5 kPa according to the Mecano method using Instron "Bluehill" software.

2. The absorbent article of claim 1, wherein said nonwoven material has a maximum strain of 65% at a pressure of 15 kPa according to the Mecano method using Instron "Bluehill" software.

3. The absorbent article according to claim 1, wherein said nonwoven material comprises substantially continuous fibres.

4. The absorbent article of claim 1, wherein the fibres of said nonwoven material have a thickness of 250-650 µm.

5. The absorbent article of claim 1, wherein the fibres of said nonwoven material are thermoplastic fibres.

6. The absorbent article of claim 1, wherein said nonwoven material has a porosity of at least 0.85 below 15 kPa, and the porosity is determined by the following equation:

Porosity=1 −[Basis weight of material $(g/cm^2)$]/
[Thickness of material at actual load (cm)×Fiber density $(g/cm^3)$].

7. The absorbent article of claim 1, wherein said fluid flow control member has a density of 0.01-0.10 $g/cm^3$.

8. The absorbent article of claim 1, wherein the fluid flow control member is located between the topsheet and the absorbent core.

9. The absorbent article of claim 1, wherein the absorbent core comprises a first absorbent core layer and a second absorbent core layer, and said first absorbent core layer is arranged between the top sheet and the second absorbent core layer, said first absorbent core layer having an opening extending through the layer.

10. The absorbent article of claim 1, wherein said fluid flow control member is made of a nonwoven material having bonded and random broken bonding points where fibres intersect.

11. The absorbent article of claim 10, wherein the material comprises at least 1, 2, or 3 broken bonding points per 1 $cm^3$.

12. The absorbent article of claim 1, wherein said fluid flow control member is made of a nonwoven material in which the fibres are bonded at points where fibres intersect.

13. The absorbent article according to claim 1, wherein said fibres are substantially continuous fibres.

14. The absorbent article of claim 1, wherein the absorbent core comprises a first absorbent core layer and a second absorbent core layer, and said fluid flow control member is located between said first and second absorbent core layers.

15. The absorbent article according to claim 1, wherein the nonwoven material has a basis weight of 541 $g/m^2$ to 900 $g/m^2$.

16. An absorbent article, the absorbent article being a personal hygiene article that is wearable by a user and has a garment-facing side and a skin facing side, comprising a liquid permeable top sheet, a liquid impermeable back sheet, and an absorbent core enclosed between the top sheet and the back sheet, and a fluid flow control member arranged between the top sheet and the back sheet, wherein said fluid flow control member is substantially free from absorbing fibres and superabsorbent material, and wherein said fluid flow control member has a thickness of 4-20 mm and is a nonwoven material comprising a three dimensional network of fibres, said fibres being randomly oriented, and having a thickness of 200-700 µm, said nonwoven material having a basis weight above 300 $g/m^2$ and less than or equal to 900 $g/m^2$, having a total free volume of at least 20 mL, and having a maximum strain of 50% at a pressure of 5 kPa according to the Mecano method using Instron "Bluehill" software.

17. The absorbent article of claim 16, wherein said fluid flow control member includes a supporting carrier layer.

* * * * *